(12) United States Patent
Katsumata

(10) Patent No.: US 10,010,301 B2
(45) Date of Patent: Jul. 3, 2018

(54) MOBILE X-RAY IMAGING DEVICE

(71) Applicant: Shimadzu Corporation, Kyoto-shi (JP)

(72) Inventor: Ryo Katsumata, Kyoto-shi (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 307 days.

(21) Appl. No.: 14/917,024

(22) PCT Filed: Sep. 6, 2013

(86) PCT No.: PCT/JP2013/074133
§ 371 (c)(1),
(2) Date: Jun. 27, 2016

(87) PCT Pub. No.: WO2015/033445
PCT Pub. Date: Mar. 12, 2015

(65) Prior Publication Data
US 2016/0287193 A1    Oct. 6, 2016

(51) Int. Cl.
*A61B 6/00*    (2006.01)
*A61B 6/10*    (2006.01)
*G05D 1/02*    (2006.01)

(52) U.S. Cl.
CPC .............. *A61B 6/4405* (2013.01); *A61B 6/102* (2013.01); *A61B 6/54* (2013.01); *G05D 1/0234* (2013.01); *G05D 2201/0206* (2013.01)

(58) Field of Classification Search
CPC ......... A61B 6/102; A61B 6/4405; A61B 6/54; A61B 6/547; G05D 1/0234; G05D 2201/0206
See application file for complete search history.

(56) References Cited

U.S. PATENT DOCUMENTS

2010/0329426 A1* 12/2010 Oda .................... A61B 6/4283
378/98.2
2014/0093051 A1* 4/2014 Nishimura ........... A61B 6/4405
378/198

(Continued)

FOREIGN PATENT DOCUMENTS

JP    2006-087595 A    9/2004
JP    2008-061944 A    3/2008

(Continued)

OTHER PUBLICATIONS

Notification of Reasons for Refusal dated Mar. 5, 2018 of corresponding Chinese Patent Application No. 201380080753.1.

*Primary Examiner* — Glen Kao
(74) *Attorney, Agent, or Firm* — Muir Patent Law, PLLC

(57) ABSTRACT

With a mobile X-ray apparatus disclosed, an operator is able to go rounds without contacting to the mobile X-ray apparatus while the mobile X-ray apparatus traveling automatically tracks the operator. Since the operator controls the mobile X-ray apparatus without contacting to the mobile X-ray apparatus, the operator is able to carry more items necessary for patient diagnosis with an operator's free hand. In addition, the mobile X-ray apparatus automatically travels while tracking the operator from behind. Accordingly, an operator's view is not obstructed, ensuring prevention of the mobile X-ray apparatus from contacting to the obstructions. Moreover, when the operator enters into a no-entry area for the mobile X-ray apparatus, it is detected that the mobile X-ray apparatus is now ready to enter into the no-entry area, and accordingly, the mobile X-ray apparatus stops its automatic tracking function. With the above configuration, the mobile X-ray apparatus allows automatic travelling while tracking the operator, and also allows automatic prevention of the mobile X-ray apparatus from entering into the no- (Continued)

entry area. As a result, rounds with the mobile X-ray apparatus are performable in a safer manner.

9 Claims, 10 Drawing Sheets

(56) References Cited

U.S. PATENT DOCUMENTS

| | | | | |
|---|---|---|---|---|
| 2014/0241504 A1* | 8/2014 | Lundstrom | .......... | A61B 6/4283 378/62 |
| 2016/0166216 A1* | 6/2016 | Igney | .................. | A61B 6/0407 356/614 |

FOREIGN PATENT DOCUMENTS

| | | |
|---|---|---|
| JP | 2010-094162 A | 4/2010 |
| JP | 2012-168602 A | 9/2012 |
| JP | 2013-514138 A | 4/2013 |
| WO | 2011/075232 A1 | 6/2011 |

* cited by examiner

Fig.6
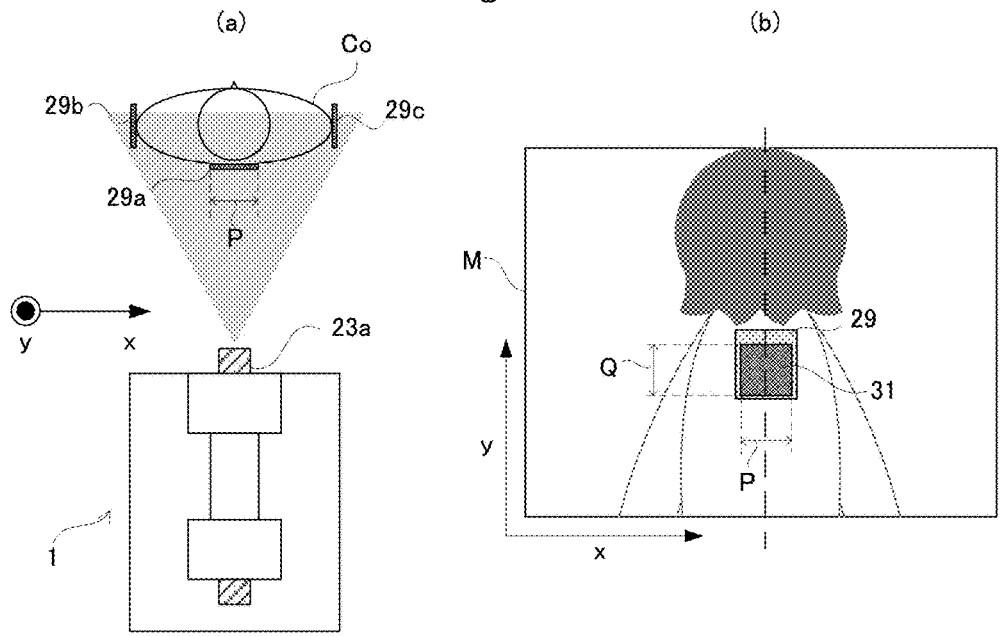
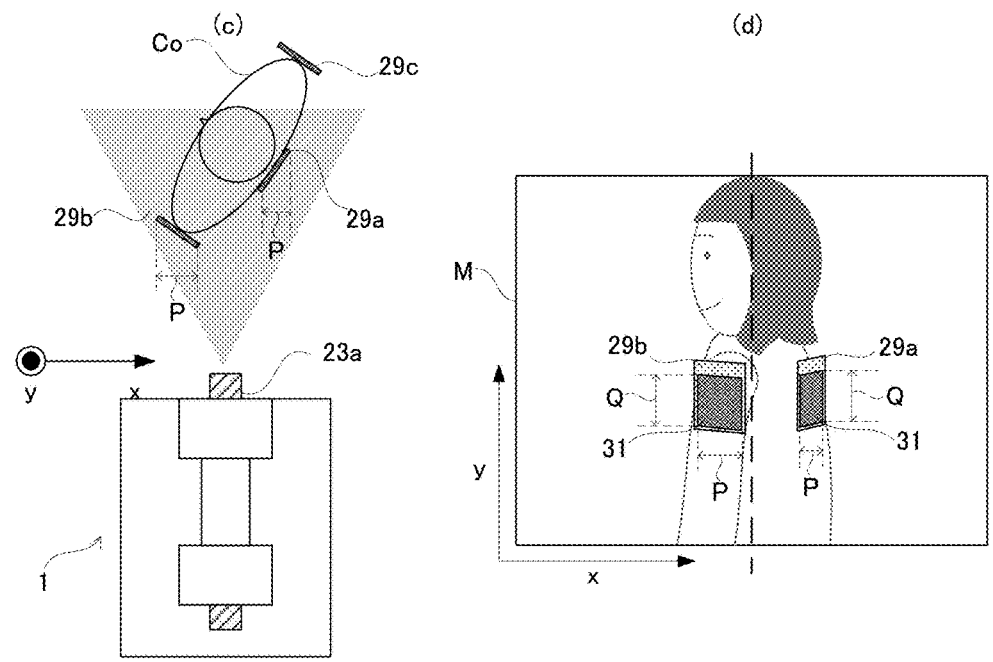

Fig.8
(a)
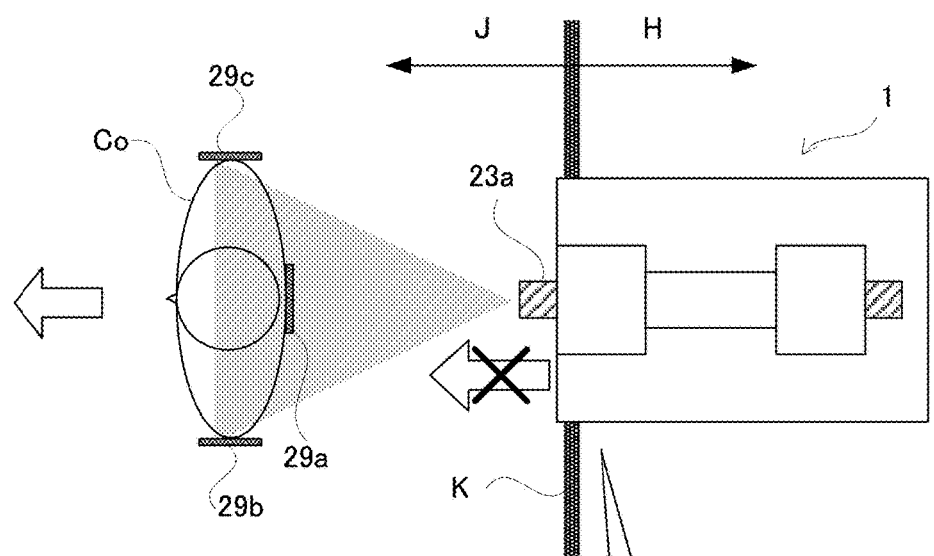
(b)
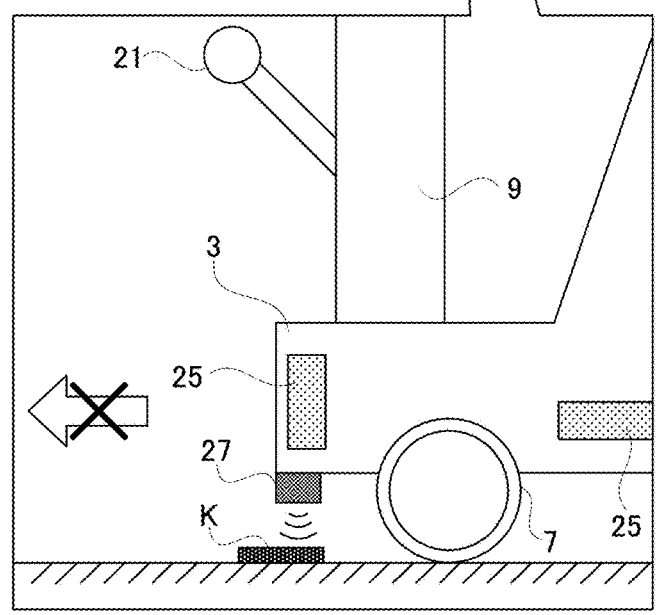

Fig.9
(a)
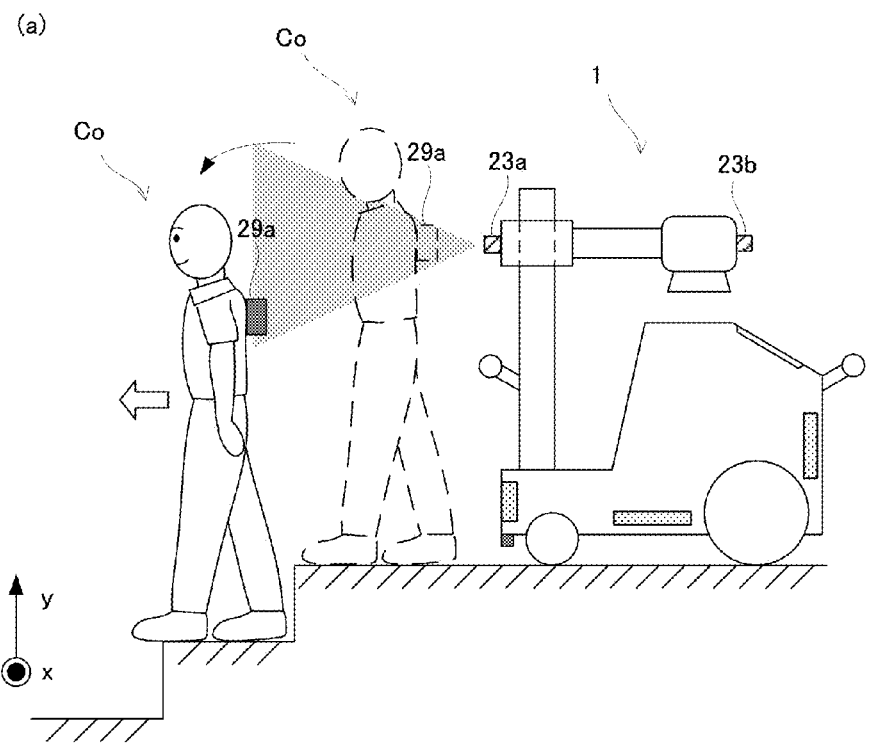
(b) BEFORE UP AND DOWN CLIMBING OF STAIRS
(c) AFTER UP AND DOWN CLIMBING OF STAIRS
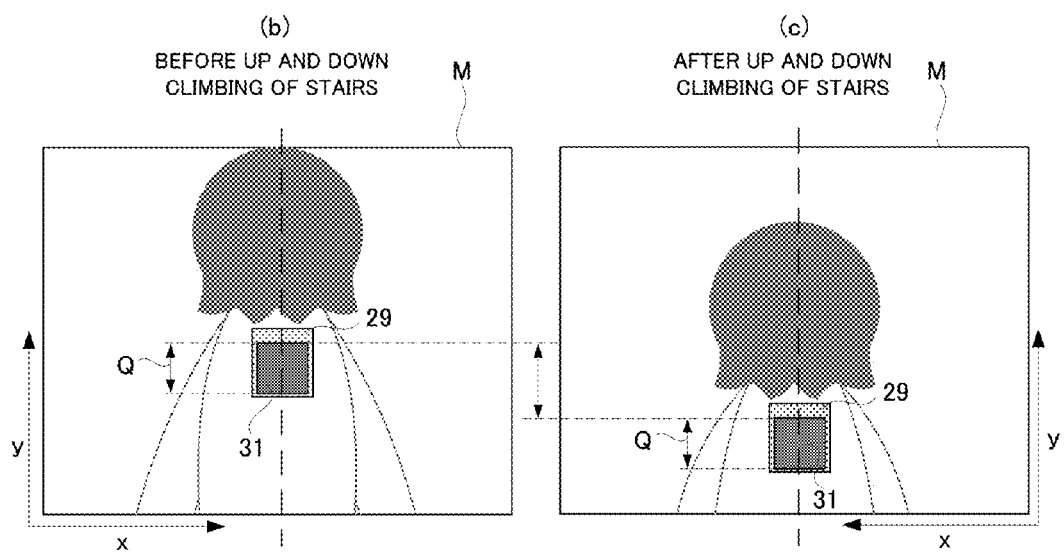

Fig.10
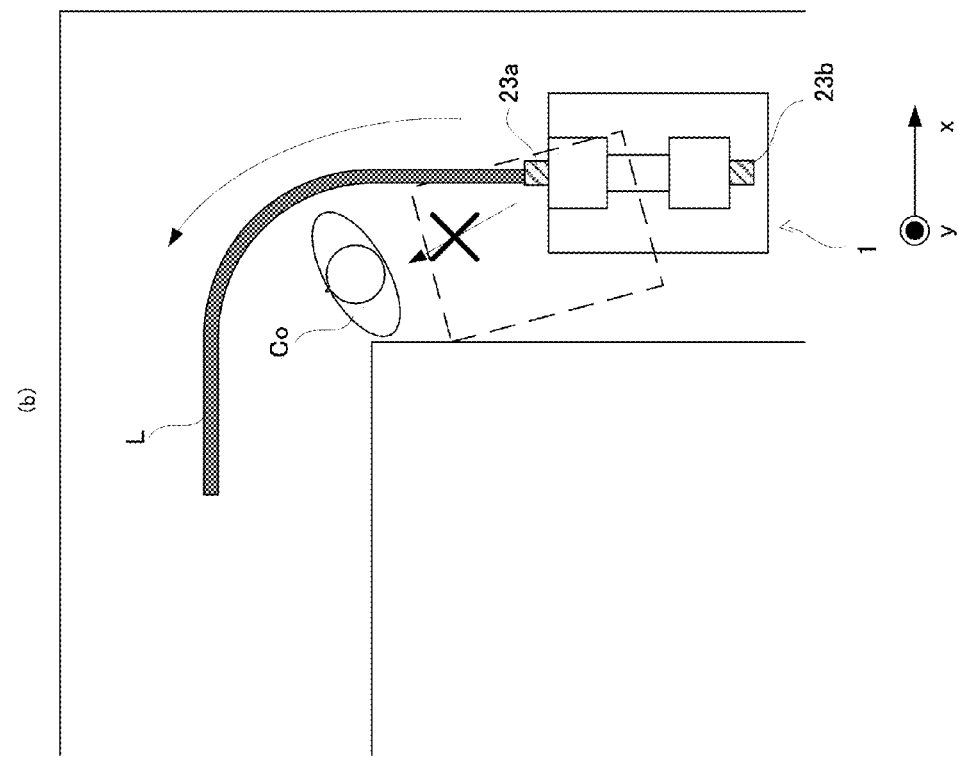
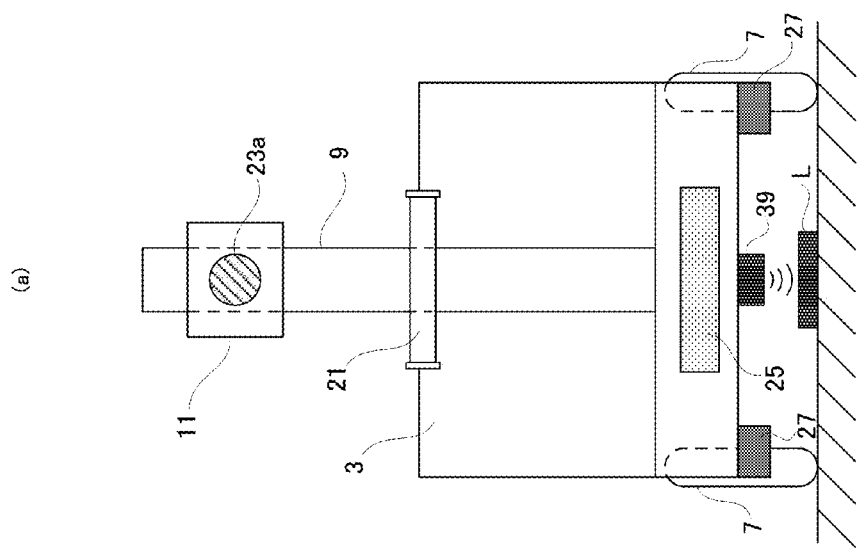

MOBILE X-RAY IMAGING DEVICE

CROSS REFERENCE TO RELATED APPLICATIONS

This application is a U.S. National Stage application under 35 U.S.C. § 371, of International Application PCT/JP2013/074133 filed on Sep. 6, 2013, which was published as WO 2015/033445 on Mar. 12, 2015. The application is incorporated herein by reference.

TECHNICAL FIELD

The present invention relates to a mobile X-ray apparatus that performs X-ray radiography to a subject.

BACKGROUND ART

In clinical practice, a patient with difficulty in moving to a radiography room sometimes undergoes round using X-ray radiography. Moreover, emergent X-ray radiography may be performed in an operating room. In the above cases, a mobile X-ray apparatus that is movable in the hospital is used as an apparatus for performing X-ray radiography to the patient.

The mobile X-ray apparatus mainly includes a main body provided with drive wheels on right and left sides thereof, an X-ray tube that applies X-rays to a subject, an arm that supports the X-ray tube on the main body such that the X-ray tube is freely movable, and operating handles. The drive wheels rotate with an electric motor in the main body. Rotating the drive wheels causes the main body to move forward/backward. A difference in rotation speed of the drive wheels on the right and left sides causes the main body to turn rightward/leftward.

The operating handles each include a plurality of pressure sensors. The pressure sensors each detect pressure applied to the operating handle by an operator for controlling rotation directions and rotation speeds of the drive wheels individually (see, for example, Patent Literature 1). Moreover, a plurality of distance sensors is provided on a back face of the main body. Even if force applied to the operating handles differs between the right side and the left side, a travelling direction of the main body is corrected appropriately in accordance with a distance between each of the distance sensors and the operator (see, for example, Patent Literature 2).

With the mobile X-ray apparatus, the operator stays frontward or rearward of the mobile X-ray apparatus while controlling the operating handles with operator's hands, and moves to a bedroom of a patient as an X-ray target (see, for example, Patent Literature 3). When moving to the patient's bedroom, the operator moves the arm appropriately to shift the X-ray tube to an optimal position for X-ray radiography. Then, a subject undergoes X-ray radiography, whereby a transmitted X-ray image is obtained. After the X-ray radiography, the operator controls the operating handles to move out from the bedroom with the mobile X-ray apparatus, and moves to a next place.

Patent Literature 1: Japanese Unexamined Patent Publication No. 2008-61944A
Patent Literature 2: Japanese Unexamined Patent Publication No. 2010-94162A
Patent Literature 3: Japanese Unexamined Patent Publication No. 2006-87595A

SUMMARY OF INVENTION

Technical Problem

However, the currently-used example with the above configuration has the following drawbacks. That is, the currently-used mobile X-ray apparatus travels while the operating handles are held with the operator's hands. Consequently, it is impossible to carry charts for rounds. In addition, when the operator follows the X-ray apparatus from behind, a large X-ray apparatus partially obstructs an operator's front view. This places a large burden on operation.

The present invention has been made regarding the state of the art noted above, and its one object is to provide a mobile X-ray apparatus that detects and automatically tracks an operator who moves frontward with safety and with less operational burden for the operator.

Solution to Problem

The present invention is constituted as stated below to achieve the above object. One aspect of the present invention provides a mobile X-ray apparatus. The mobile X-ray apparatus includes a carriage of which a main body of the X-ray apparatus is on board, drive wheels that move the carriage, a label attached to an operator, a label detector that detects the label, and a label tracking controller that controls driving of the drive wheels such that the carriage tracks the label in accordance with a result detected by the label detector.

With the mobile X-ray apparatus according to the aspect of the present invention, the label tracking controller controls driving of the drive wheels such that the carriage tracks the label in accordance with the result identified by the label detector. The label is attached to the operator. Accordingly, the mobile X-ray apparatus tracks the operator with the label. Consequently, the operator allows rounds without any contact to the mobile X-ray apparatus while the automatically travelling mobile X-ray apparatus tracks the operator.

Since the operator allows operation of the mobile X-ray apparatus without any contact thereto, operator's hands are free during the rounds. That is, the operator is able to carry more items, such as charts and diagnosis tools, necessary for patient diagnosis upon the rounds. As a result, this achieves efficient and effective diagnosis in the rounds.

In addition, the mobile X-ray apparatus automatically travels while tracking the operator from behind. That is, a large mobile X-ray apparatus is prevented from obstructing an operator's view. Consequently, the operator allows confirmation of patients and obstructions in advance that come and go, ensuring prevention of the mobile X-ray apparatus from contacting to the obstructions.

Moreover, in the aspect of the present invention, it is preferred that the label tracking controller stops the driving of the drive wheels when the label detector detects that the label is moved vertically for a given period of time. When the operator climbs up and down stairs, the attached label is moved vertically along with up and down climbing of the stairs by the operator. That is, when the label is moved vertically for a given period of time, it is determined that the operator climbs up and down the stairs. If the mobile X-ray apparatus continuously tracks the operator who climbs up and down stairs to travel to the stairs, the mobile X-ray apparatus may fall down from the stairs. Accordingly, when the label detector detects that the label is moved vertically for a given period of time, the label tracking controller stops the driving of the drive wheels, whereby automatic tracking is interrupted. With such a configuration, the mobile X-ray apparatus allows stop of the automatic tracking even when the operator unintentionally climbs up and down the stairs.

Moreover, it is preferred that the aspect of the present invention further includes an alert sounding device that sounds an alert, and the alert sounding device sounds the alert when the label detector detects no label for a given period of time. In this case, the label detector detects no label. Accordingly, the mobile X-ray apparatus determines it impossible to track the operator, and stops automatic tracking. However, the operator directed frontward has difficulty in noticing that the mobile X-ray apparatus stops the automatic tracking. Then, the alert sounding device sounds the alert, whereby the operator is able to notice easily that the mobile X-ray apparatus has stopped the automatic tracking.

Moreover, it is preferred that the aspect of the present invention further includes a laid object detector that detects a laid object that is laid on the floor, and the label tracking controller stops the driving of the drive wheels when the laid object detector detects the laid object. The laid object, such as a metal tape, is laid on a boundary of a no-entry area so as to prevent the mobile X-ray apparatus from entering into a specific area. Detecting the laid object by the laid object detector allows determination that the mobile X-ray apparatus has entered into the no-entry area. Then, the label tracking controller stops the driving of the drive wheels, whereby the automatic tracking is interrupted. Such a configuration achieves automatic prevention of the mobile X-ray apparatus from entering into the no-entry area.

Moreover, it is preferred in the aspect of the present invention that the alert sounding device sounds the alert when the laid object detector detects the laid object. When the laid object detector detects the laid object, the mobile X-ray apparatus has already entered into the no-entry area. Accordingly, the label tracking controller stops the driving of the drive wheels, whereby the automatic tracking is interrupted. At this time, the alert sounding device sounds the alert. Consequently, the operator directed frontward is able to notice easily that the mobile X-ray apparatus has stopped the automatic tracking. This allows avoidance of the risk that the operator leaves the mobile X-ray apparatus.

Moreover, it is preferred that the aspect of the present invention further includes an obstruction detector that detects contact of the carriage to an obstruction, and the label tracking controller stops the driving of the drive wheels when the obstruction detector detects the contact of the carriage to the obstruction. When the carriage contacts the obstruction, the obstruction detector rapidly detects the contact. In order to prevent successive automatic tracking after the contact to the obstruction, the label tracking controller stops the driving of the drive wheels and interrupts the automatic tracking when the obstruction detector detects the contact of the carriage to the obstruction. With such a configuration, the rounds with the mobile X-ray apparatus are performable in a safer manner.

Moreover, it is preferred in the aspect of the present invention that the alert sounding device sounds the alert when the obstruction detector detects the contact of the carriage to the obstruction. When the obstruction detector detects the contact to the obstruction, the label tracking controller stops the driving of the drive wheels and interrupts the automatic tracking in order to prevent successive automatic tracking. At this time, the alert sounding device sounds the alert. Consequently, the operator directed frontward is able to notice easily that the mobile X-ray apparatus has stopped the automatic tracking. This achieves prevention of the operator from leaving the mobile X-ray apparatus.

Moreover, it is preferred that the aspect of the present invention further includes a moving route detector that detects a moving route of the carriage set in advance, and the label tracking controller stops the driving of the drive wheels so as to travel along the moving route when the moving route detector detects the moving route.

At this time, the moving route of the carriage is determined in advance, and a colored tape is laid on the floor to indicate the moving route. The moving route detector detects the laid colored tape, thereby identifying a route along which the carriage is to be moved. Then the label tracking controller controls the drive wheels so as to travel along the moving route. The label tracking controller assigns high priority to the moving route detected with the moving route detector, and performs control to travel along the route indicated with the colored tape. Consequently, in the area with the laid colored tape, the mobile X-ray apparatus travels along the route indicated with the colored tape regardless of operator's motion even when the operator walks frontward while tottering rightward/leftward.

For instance, when the operator turns on a corridor, the operator often turns along the wall. In this case, if the mobile X-ray apparatus travels while tracking the label, the mobile X-ray apparatus has the higher risk of collision with the wall while tracking the operator who walks along the wall. Accordingly, a route for safe travelling of the mobile X-ray apparatus is indicated with the colored tape on the area of the floor, such as a corner or an intersection of the corridor, that is especially necessary for safe travelling. With such a configuration, the mobile X-ray apparatus allows travelling along a steady route even when the operator moves unstably at the corner or the intersection of the corridor.

The mobile X-ray apparatus allows automatic travelling while tracking the operator in the area without any moving route. Consequently, the mobile X-ray apparatus allows travelling along a safer route at the corner or the intersection of the corridor while automatically tracking.

Moreover, it is preferred in the aspect of the present invention that the alert sounding device is a portable terminal. The operator carries the portable terminal. Accordingly, when the portable terminal sounds the alert, the operator is able to catch the alert more positively. This ensures eliminated possibility that the operator fails to catch the alert to leave the mobile X-ray apparatus that stops the automatic tracking. Moreover, even when the automatic tracking of the mobile X-ray apparatus is interrupted, the operator is able to interrupt the automatic tracking rapidly using the portable terminal that the operator carries. Consequently, the mobile X-ray apparatus is operatable in a safer manner while dealing with an unforeseen situation that needs interruption of the automatic tracking.

Advantageous Effects of Invention

With the mobile X-ray apparatus according to the aspect of the present invention, the operator is able to go rounds with a label tracking controller without contacting to the mobile X-ray apparatus while the mobile X-ray apparatus travelling automatically tracks the operator. Since the operator controls the mobile X-ray apparatus without contacting to the mobile X-ray apparatus, the operator is able to carry more items necessary for patient diagnosis with an operator's free hand. As a result, this achieves efficient and effective diagnosis in the rounds. In addition, the mobile X-ray apparatus automatically travels while tracking the operator from behind. Accordingly, an operator's view is not obstructed. The operator allows confirmation of patients and obstructions in advance that come and go, ensuring prevention of the mobile X-ray apparatus from contacting to the obstructions. Moreover, when the operator enters into an area dangerous for the mobile X-ray apparatus, the label tracking controller detects the entering to stop an automatic tracking function of the mobile X-ray apparatus. With such a configuration, the mobile X-ray apparatus allows automatic travelling while tracking the operator, and also allows automatic prevention of the mobile X-ray apparatus from entering into the no-entry area. As a result, the rounds with the mobile X-ray apparatus are performable in a safer manner.

BRIEF DESCRIPTION OF DRAWINGS

FIG. 6 schematically illustrates how to calculate an operator's body direction relative to the mobile X-ray apparatus of the Embodiment 1, FIG. 6(a) being a plan view when the operator is directed behind to the mobile X-ray apparatus, FIG. 6(b) illustrating an image captured by a video camera in FIG. 6(a), FIG. 6(c) is a plan view when the operator is directed ahead on the left, and FIG. 6(d) illustrating an image captured by the video camera in FIG. 6(c).

FIG. 8 schematically illustrates a function of preventing the mobile X-ray apparatus of the Embodiment 1 from entering into a no-entry area, FIG. 8(a) a plan view thereof, and FIG. 8 (b) a side view thereof.

FIG. 9 schematically illustrates a function of preventing the mobile X-ray apparatus of the Embodiment 1 from entering into stairs, FIG. 9(a) a side view thereof, and FIGS. 9(b) and 9(c) each an image captured by a video camera.

FIG. 10 schematically illustrates a mobile X-ray apparatus according to Preferred Embodiment 2, FIG. 10(a) a front view thereof, and FIG. 10(b) a schematic plan view of the mobile X-ray apparatus turning a corner along a route indicated by a colored tape.

DESCRIPTION OF EMBODIMENTS

Embodiment 1

Figure 1:
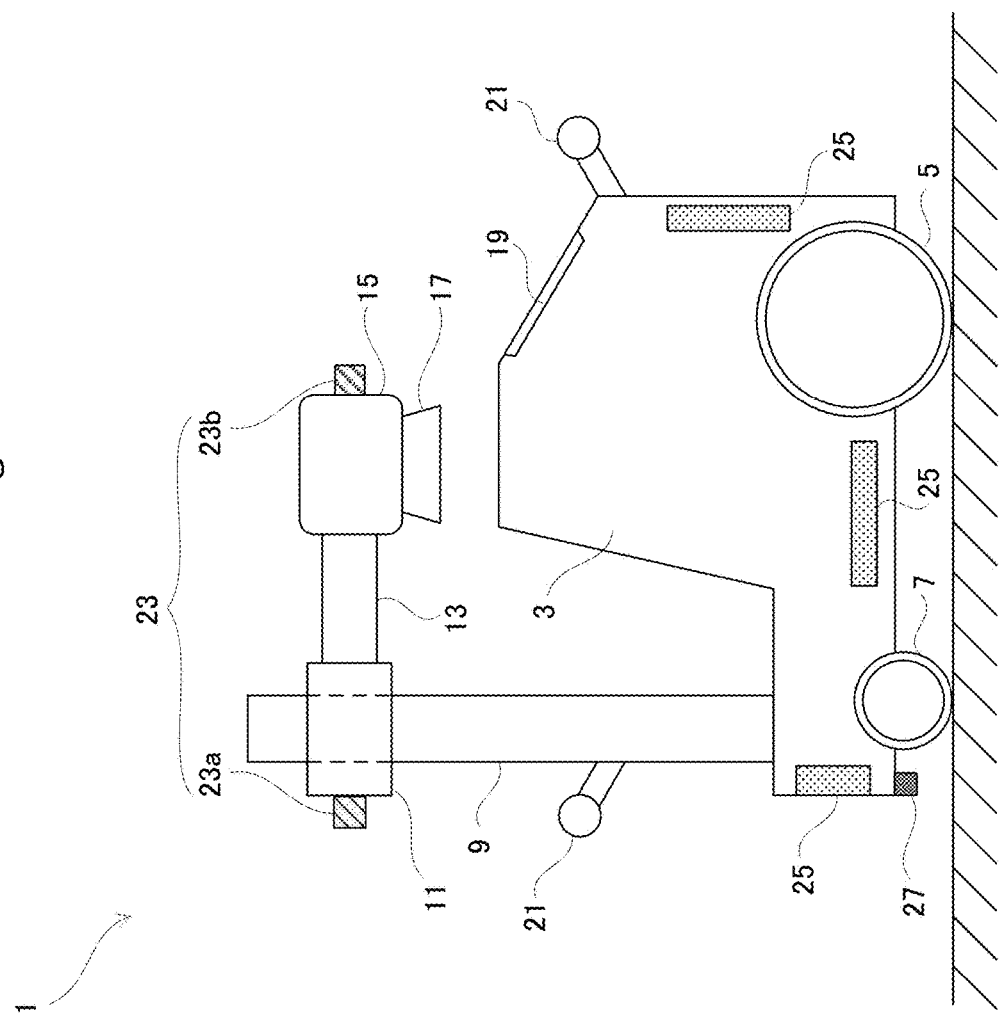
FIG. 1 is a schematic side view of a mobile X-ray apparatus according to Preferred Embodiment 1 of the present invention.

The following describes in detail Preferred Embodiment 1 of the present invention with reference to drawings.

<Overall Configuration>

A mobile X-ray apparatus 1 according to Embodiment 1 includes a carriage 3, drive wheels 5, front wheels 7, a strut 9, a holder mechanism 11, a horizontal arm 13, an X-ray tube 15, a collimator 17, a console panel 19, operating handles 21, a video camera 23, contact sensors 25, and a metal sensor 27.

The drive wheels 5 are disposed on the carriage 3 on rear lower parts thereof on right and left sides. An electric motor inside the carriage 3 rotates the drive wheels 5. Rotating the drive wheels 5 causes the carriage 3 to move forward/backward. A difference in rotation speed of the right and left drive wheels 5 causes the carriage 3 to turn rightward/leftward. The front wheels 7 are disposed on the carriage 3 on front lower parts thereof on right and left sides. The front wheels turn rightward/leftward along with a turning direction of the carriage 3.

The strut 9 is erected on a front part of the carriage 3, and is configured to rotate around a vertical axis. The holder mechanism 11 is disposed on the strut 9, and is configured to move vertically. The holder mechanism 11 is also connected to a first end of the horizontal arm 13. The horizontal arm 13 is extendible and contractible in a horizontal direction. The X-ray tube 15 is disposed on a second end of the horizontal arm 13. The X-ray tube 15 is rotatable around the axis of the horizontal arm 13, and emits X-rays depending on X-ray radiography conditions set in advance.

The collimator 17 is disposed on a lower part of the X-ray tube 15, and collimates X-rays emitted from the X-ray tube 15 in a cone shape for adjusting an irradiation field with X-rays. The console panel 19 includes an operating unit for setting the X-ray radiography conditions such as an imaging time and a switch for X-ray radiography. The operating handles 21 are disposed on front and rear parts of the mobile X-ray apparatus 1. The operating handles 21 each include a plurality of pressure sensors inside thereof. The pressure sensors each detect pressure to be applied to the operating handle 21 and control rotation speeds of the drive wheels 5 when the operator grips the operating handle 21 and operates the carriage 3. Since arrangement of the pressure sensors are described in detail in the above Patent Literature 1 and the like, further description thereof is to be omitted.

The mobile X-ray apparatus 1 includes the video camera 23 with two video cameras 23a and 23b, one video camera 23a on the holder mechanism 11 and the other video camera 23b on the collimator 17. The video camera 23a captures a front side of the mobile X-ray apparatus 1 at any time, whereas the video camera 23b captures a rear side of the mobile X-ray apparatus 1 at any time. The contact sensors 25 are provided on the exterior of the carriage 3 on the right and left thereof for detecting contact to obstructions. The metal sensor 27 is disposed on a front bottom part of the carriage 3 for detecting a metal tape on the floor. Here, the video camera 23 corresponds to the label detector in the present invention.

Figure 2:
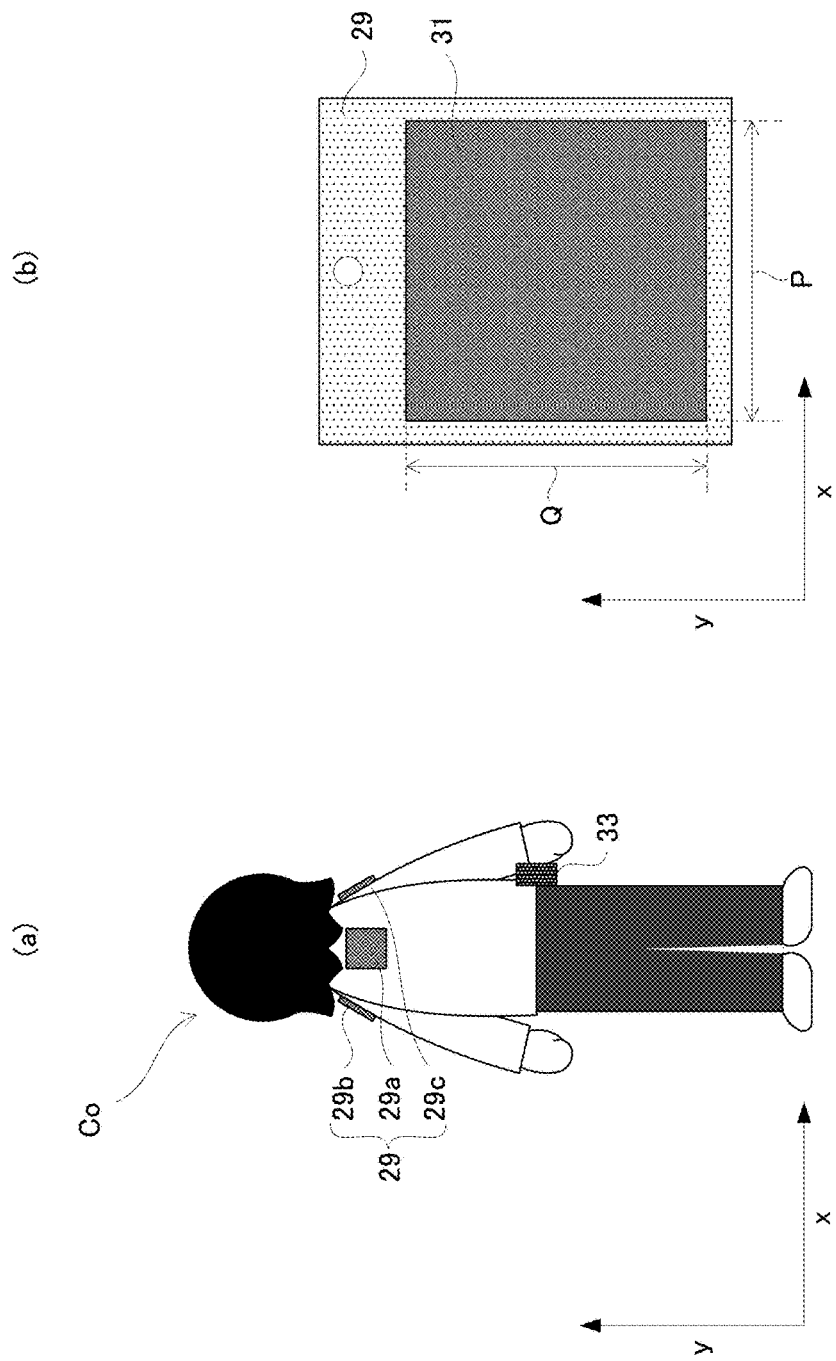
FIG. 2(a) schematically illustrates attachment to an operator upon using the mobile X-ray apparatus according to the Embodiment 1.
FIG. 2(b) is a front view of a marker according to the Embodiment 1.

As illustrated in FIG. 2(a), an operator Co has a marker 29 attached to the back, right and left shoulders individually when moving the mobile X-ray apparatus. It is assumed that the marker 29 attached to the back is denoted by a marker 29a, the marker 29 attached to the left shoulder by a marker 29b, and the marker 29 attached to the right shoulder by a marker 29c. As illustrated in FIG. 2(b), the marker 29 has a two-dimensional code 31 printed thereon, which differs from one another. Here, it is assumed that the two-dimensional code 31 has a length in an x-direction denoted by P, and a length in a y-direction denoted by Q. In Embodiment 1, the length P is equal to the length Q. The marker 29 is attached to the operator Co with a safety-pin and the like on the operator's cloth so as to visually confirm the two-dimensional code 31. The operator Co carries a small input-output terminal 33. Here, the marker 29 corresponds to the label in the present invention. The input-output terminal 33 corresponds to the alert sounding device in the present invention.

Figure 3:
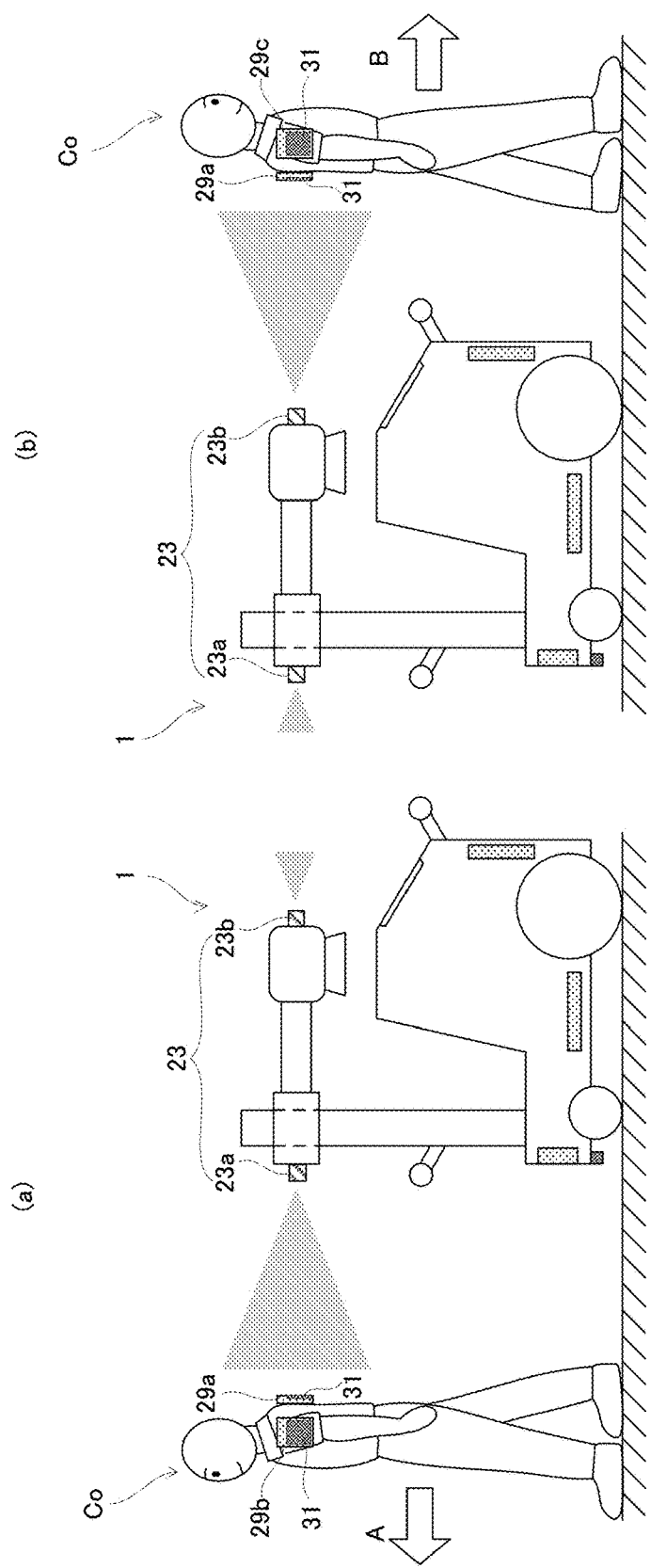
FIG. 3(a) is a schematic side view of automatic tracking of the operator who moves frontward of the mobile X-ray apparatus according to the Embodiment 1.
FIG. 3(b) is a schematic side view of automatic tracking of the operator who moves rearward of the mobile X-ray apparatus according to the Embodiment 1.

FIG. 3 schematically illustrates automatic tracking of the mobile X-ray apparatus 1. As illustrated in FIG. 3(a), when the operator Co in front of the mobile X-ray apparatus 1 moves in a direction indicated by an arrow A, the video camera 23a captures the marker 29a on the back of the operator Co. Then, the mobile X-ray apparatus 1 automatically travels in the direction by the arrow A while tracking the operator Co in accordance with a video of the two-dimensional code 31 on the marker 29a.

As illustrated in FIG. 3(b), when the operator Co behind the mobile X-ray apparatus 1 moves in a direction indicated by an arrow B, the video camera 23b captures the marker 29a. Then, the mobile X-ray apparatus 1 automatically travels in the direction indicated by the arrow B while tracking the operator Co in accordance with a video of the two-dimensional code 31. Consequently, the mobile X-ray apparatus 1 allows automatic tracking to the operator Co in both cases when the operator Co is in front of and behind the mobile X-ray apparatus 1.

<Description of Function Block Diagram>

Figure 4:
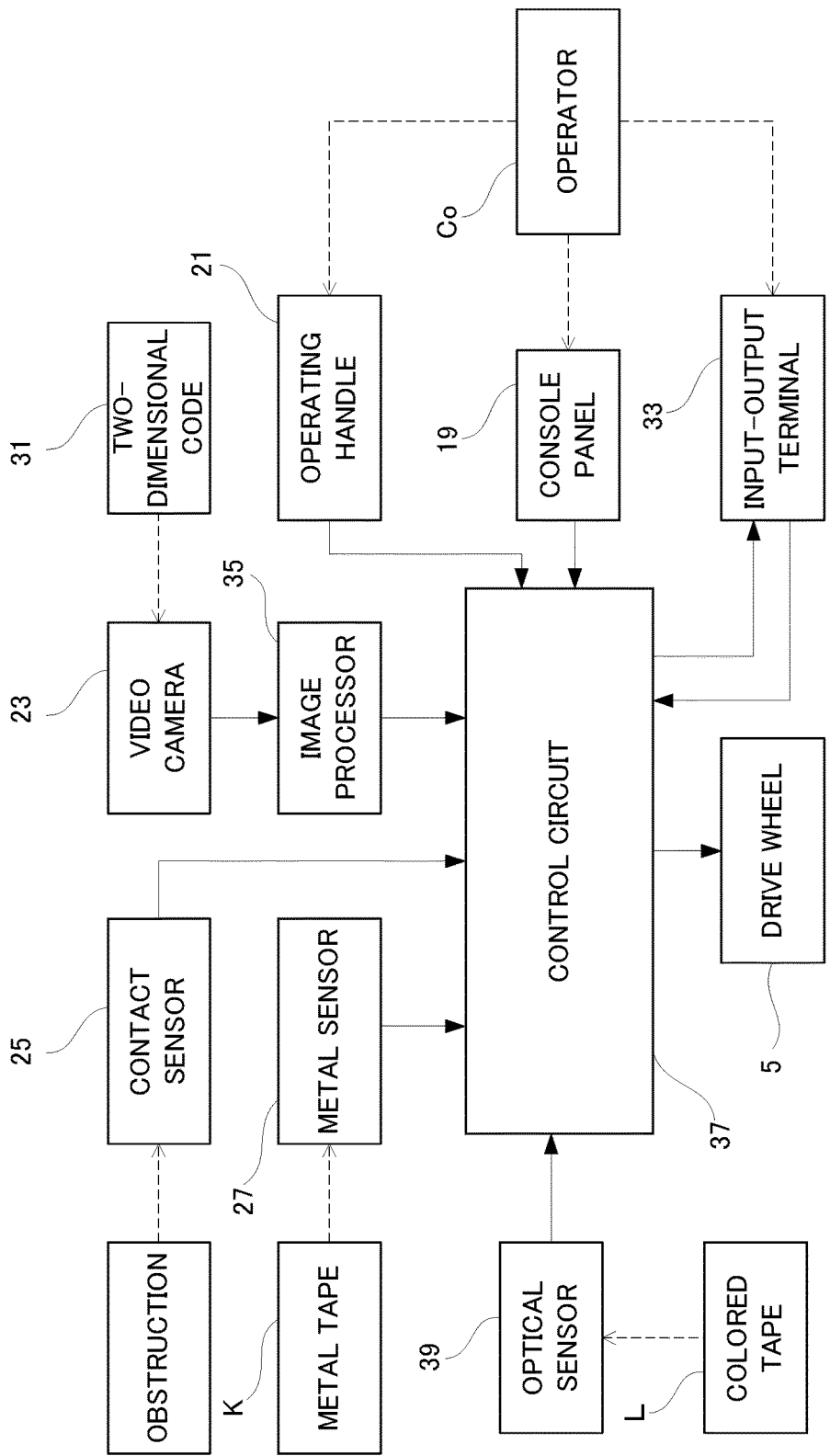
FIG. 4 is a functional block diagram of the mobile X-ray apparatus according to the Embodiment 1.

The following describes a block diagram of the mobile X-ray apparatus 1 with reference to FIG. 4. The mobile X-ray apparatus 1 includes an image processor 35 and a control circuit 37. The image of the marker 29 captured by the video camera 23 is transmitted to the image processor 35. The image processor 35 calculates a position and a direction of the operator Co based on the two-dimensional code 31 shown up on the image, and outputs a signal to the control circuit 37 in accordance with the calculated result. The control circuit 37 controls the rotation speeds of the drive wheels 5 in accordance with the outputted signal. Then the mobile X-ray apparatus 1 moves forward/backward, stops, or turns rightward/leftward in accordance with the control of the drive wheels 5. The control circuit 37 corresponds to the label tracking controller in the present invention.

When the video camera 23 captures no marker 29 for a given period of time, the image processor 35 outputs a signal to the control circuit 37. The control circuit 37 performs control to stop rotation of the drive wheels 5 in accordance with the signal, and simultaneously outputs a signal to the input-output terminal 33. The input-output terminal 33 sounds an alert in accordance with the signal for notifying the operator Co that the automatic tracking of the mobile X-ray apparatus 1 is impossible.

The contact sensor 25 detects the contact to the obstruction, and outputs a signal to the control circuit 37. The control circuit 37 performs control to stop the rotation of the drive wheels 5, and simultaneously outputs a signal to the input-output terminal 33. The input-output terminal 33 sounds an alert in accordance with the signal for notifying the operator Co that the mobile X-ray apparatus 1 has contacted the obstruction. Here, the contact sensor 25 corresponds to the obstruction detector in the present invention.

The metal sensor 27 detects the metal tape laid on the floor, and outputs a signal to the control circuit 37. The control circuit 37 performs control to stop the rotation of the drive wheels 5 in accordance with the signal, and simultaneously outputs a signal to the input-output terminal 33. The input-output terminal 33 sounds an alert in accordance with the signal for notifying the operator Co that the mobile X-ray apparatus 1 has entered into the no-entry area. Here, the metal sensor 27 corresponds to the laid object detector in the present invention.

<Description of Automatic Tracking Function>

The following describes an automatic tracking function of the mobile X-ray apparatus according to Embodiment 1 that detects and tracks the operator. Hereinafter, a condition in which the automatic tracking function is in action is referred to as an automatic tracking mode. It is assumed as illustrated in FIG. 3(a) that the operator goes rounds while walking in front of the mobile X-ray apparatus.

Figure 5:
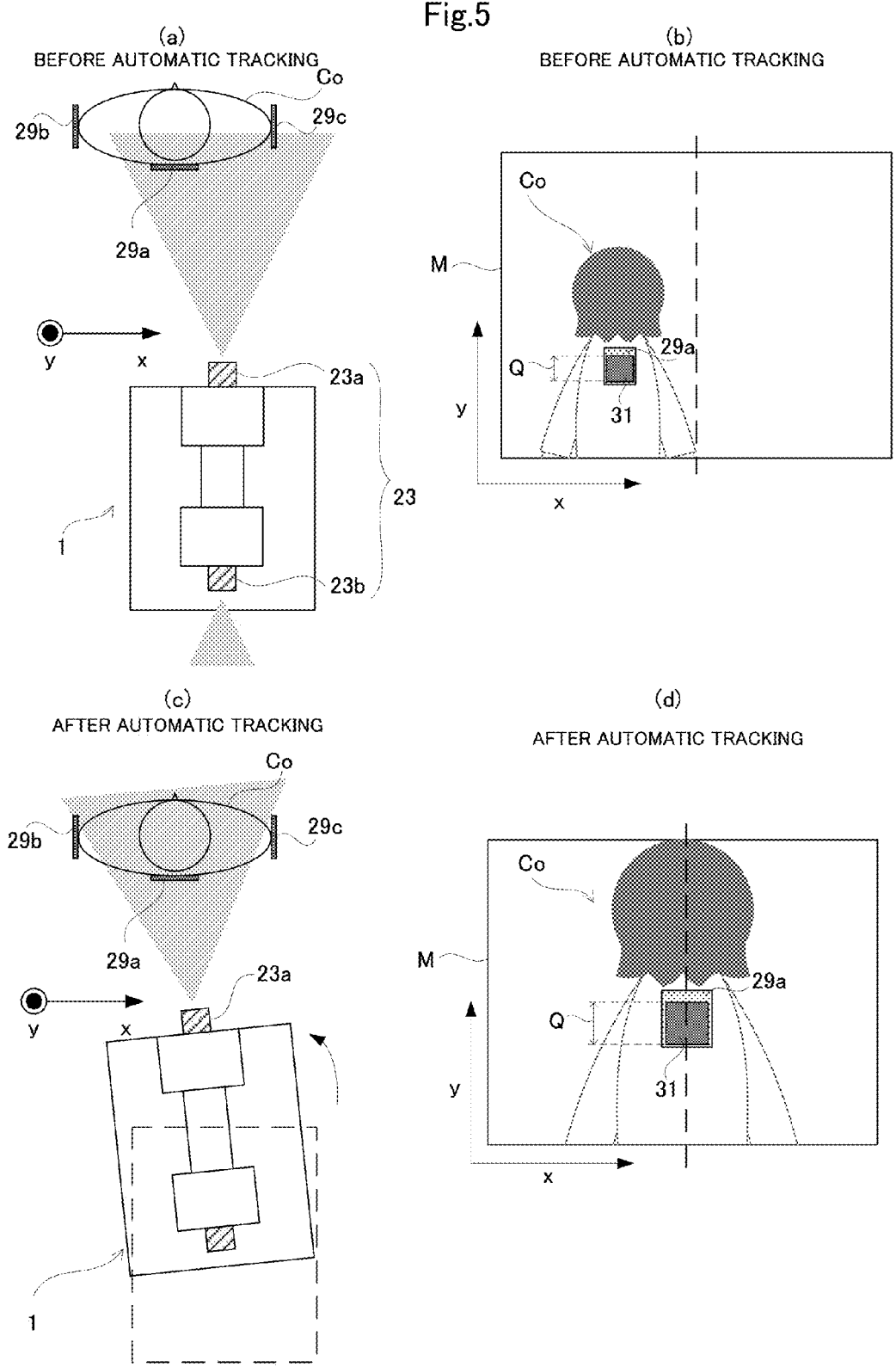
FIG. 5 schematically illustrates how to calculate an operator's position relative to the mobile X-ray apparatus of the Embodiment 1, FIG. 5(a) being a plan view when the mobile X-ray apparatus is away from the operator, FIG. 5(b) illustrating an image captured by a video camera in FIG. 5(a), FIG. 5(c) being a plan view when the mobile X-ray apparatus approaching the operator, and FIG. 5(d) illustrating an image captured by the video camera in FIG. 5(c).

In the automatic tracking mode, the video camera 23 operates to capture an image. As illustrated in FIG. 5(a), the operator Co walks in front of the mobile X-ray apparatus 1. Accordingly, as illustrated in FIG. 5(b), the video camera 23a captures the image on which the marker 29a on the back of the operator Co and the two-dimensional code 31 with the marker 29a are shown up. Hereinafter, the image captured by the video camera 23a is referred to as an image M.

The image M is transmitted to the image processor 37. The image processor 37 identifies the two-dimensional code 31 in the image M. Then, three items are calculated based on a size and a coordinate of the two-dimensional code 31 shown up on the image M. The three are a distance between the operator Co and the mobile X-ray apparatus 1, a coordinate in an x-direction of the operator Co relative to the mobile X-ray apparatus 1, and a direction of the operator Co.

Firstly, the distance between the operator Co and the mobile X-ray apparatus 1 are calculated from a length of the two-dimensional code 31 shown up on the image in y-direction, i.e., a length Q. Specifically, as illustrated in FIG. 5(a), when the operator Co is spaced away from the mobile X-ray apparatus 1, the length Q of the two-dimensional code 31 shown up on the image is small as in FIG. 5(b). When the operator Co is close to the mobile X-ray apparatus 1 as in FIG. 5(c), the length Q of the two-dimensional code 31 shown up on the image is large as in FIG. 5(d).

The image processor 35 controls the rotation speeds of the drive wheels 5 via the control circuit 37 such that the length Q of the two-dimensional code 31 shown up on the image takes a reference value set in advance. When the length Q is smaller than the reference value, the image processor 35 determines that the operator Co is excessively spaced away from the mobile X-ray apparatus 1, and outputs a signal to the control circuit 37. The control circuit 37 outputs a control signal to the drive wheels 5 in accordance with the signal to rotate the drive wheels 5. Rotating the drive wheels 5 causes the mobile X-ray apparatus 1 to start automatic travelling and track the operator Co.

In contrast to this, when the length Q is larger than the reference value, the image processor 35 determines that the mobile X-ray apparatus 1 is excessively close to the operator Co, and outputs a signal to the control circuit 37. The control circuit 37 outputs a control signal to the drive wheels 5 in accordance with the signal to stop rotation of the drive wheels 5. The rotation of the drive wheels 5 stops, whereby the mobile X-ray apparatus 1 is spaced away from the moving operator Co by an appropriate distance. With the above configuration, the mobile X-ray apparatus 1 allows automatic traveling at a constant distance to the operator Co while tracking the operator Co moving frontward.

Then, the coordinate of the operator Co in the x-direction relative to the mobile X-ray apparatus 1 is calculated from the coordinate of the two-dimensional code 31 in the x-direction shown up on the image. For instance, when the operator Co is present on the left frontward of the mobile X-ray apparatus 1 as in FIG. 5(a), the two-dimensional code 31 is shown on the left of the image M as in FIG. 5(b).

The image processor 35 controls the rotation speeds of the drive wheels 5 such that the two-dimensional code 31 shown in the image M is located constantly at the center in the x-direction. When the operator Co is present on the left frontward of the mobile X-ray apparatus 1, a rotation speed of the right drive wheel 5 is higher than a rotation speed of the left drive wheel 5. As a result, as illustrated in FIG. 5(d), the mobile X-ray apparatus 1 allows traveling in a left frontward direction so as to track the operator Co.

Then, the direction of the operator Co is calculated from types of the two-dimensional code 31 shown up on the image, and a ratio of the length P and the length Q of the two-dimensional code 31 shown up on the image M. When the back of the operator Co faces to the mobile X-ray apparatus 1 as illustrated in FIG. 6 (a), the two-dimensional code 31 of the marker 29a is shown up on the image M, but two-dimensional codes 31 of the marker 29b and the marker 29c are not shown. Since the video camera 23a captures the two-dimensional code 31 of the marker 29a from a front side, the length P is substantially equal to the length Q as in FIG. 6 (b).

In contrast to this, when the operator Co is directed leftward relative to a traveling direction of the mobile X-ray apparatus 1 as in FIG. 6 (c), the two-dimensional code 31 of the marker 29b is shown up on the image M in addition to the two-dimensional code 31 of the marker 29a as in FIG. 6 (d). Moreover, since the operator Co is directed leftward, the video camera 23a captures the two-dimensional code 31 of the marker 29a diagonally. As a result, the two-dimensional code 31 of the marker 29a shown up on the image M has the length P smaller than the length Q.

A ratio of the length P and the length Q in the marker 29a becomes smaller and a ratio of the length P and the length Q in the marker 29b becomes larger as the operator Co is directed leftward relative to the traveling direction of the mobile X-ray apparatus 1. When the operator Co is directed rightward, a two-dimensional code of the marker 29c is shown up on the image M. Consequently, the direction of the operator Co is able to be calculated from the types of the marker 29 shown up on the image M and the ratio of the length P and the length Q in the two-dimensional code 31.

Figure 7:
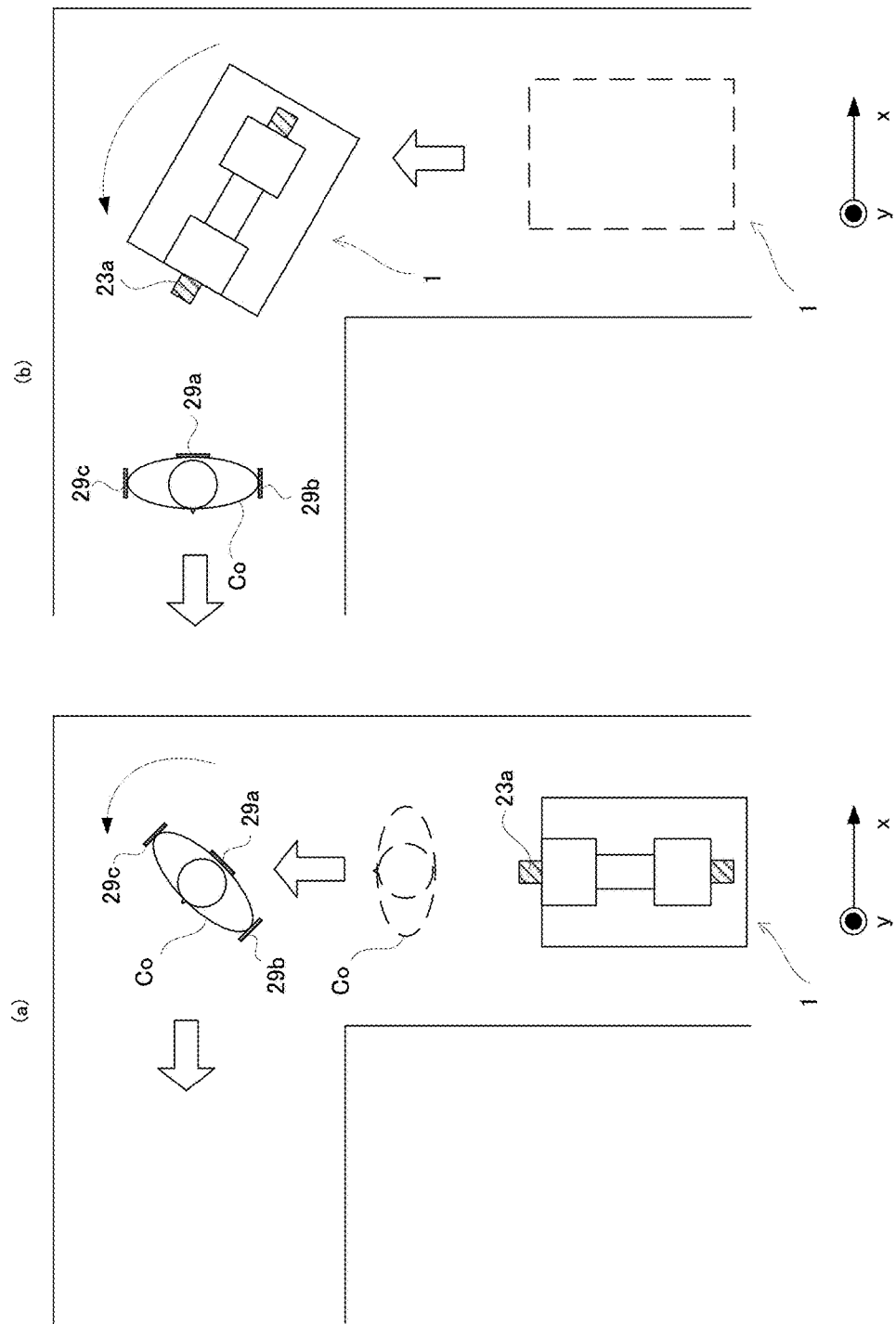
FIG. 7 illustrates a plan view of a function of the mobile X-ray apparatus that tracks the operator who turns a corner in the Embodiment 1, FIG. 7(a) a plan view that the mobile X-ray apparatus tracks the operator turning the corner, and FIG. 7(b) a plan view that the mobile X-ray apparatus tracks the operator having turned the corner and turns around at the corner.

For instance, when the operator Co turns the corner to the left, the operator Co moves straight from a position by dotted lines to a position by solid lines in FIG. 7(a), and then turns the operator's body to the left, and thereafter moves in the left direction. Accordingly, the image processor 35 calculates a position where the operator Co turns the operator's body to the left in accordance with the two-dimensional code 31 shown up on the image M, and outputs a signal to the control circuit 37. The control circuit 37 controls the rotation speeds of the drive wheels 5 so as to move the mobile X-ray apparatus 1 straight from a position by dotted lines to a position by solid lines in FIG. 7(b) and to turn to the left. The mobile X-ray apparatus 1 having turned to the left captures the operator Co having moved to the left with the video camera 23a, and travels so as to track the operator Co. The above operation allows the mobile X-ray apparatus 1 to track the operator Co turning the corner.

<Identification of No-Entry Area>

The following describes a function that the mobile X-ray apparatus according to Embodiment 1 identifies the no-entry area for cancelling the automatic tracking mode.

As illustrated in FIG. 8(a), a metal tape K is laid in advance on a boundary between an entry area H and a no-entry area J of the mobile X-ray apparatus 1. The mobile X-ray apparatus 1 includes a metal sensor 27 on the bottom face thereof. Consequently, when the mobile X-ray apparatus 1 enters from the entry area H to the no-entry area J, the metal sensor 27 detects the metal tape K laid on the floor as in FIG. 8(b).

Upon detection of the metal tape K, the metal sensor 27 outputs a signal to the control circuit 37. The control circuit 37 stops the rotation of the drive wheels 5 in accordance with the outputted signal, and simultaneously outputs a signal to the input-output terminal 33. The input-output terminal 33 sounds an alert in accordance with the signal outputted from the control circuit 37 for notifying the operator Co that the automatic tracking mode is cancelled due to entering into the no-entry area J. The above configuration allows prevention of the mobile X-ray apparatus 1 from entering into the no-entry area J.

However, only the above configuration may not possibly secure satisfactory safety of the mobile X-ray apparatus 1. The following case is included as one example thereof that the mobile X-ray apparatus 1 travels to the stairs. When the mobile X-ray apparatus travels to the stairs while tracking the operator Co who climbs up and down the stairs, a large mobile X-ray apparatus 1 may probably fall down from the stairs. In this case, the laid metal tape K in front of the stairs is insufficient for stopping the mobile X-ray apparatus 1, and accordingly the mobile X-ray apparatus 1 may possibly travel to the stairs and fall down from the stairs. Then, a function is necessary instead of the metal sensor 27 for the mobile X-ray apparatus 1 to identify that the operator Co goes the stairs and stops the automatic tracking.

When the operator Co climbs up and down the stairs, the operator Co moves from a position by dotted lines to a position by solid lines as in FIG. 9(a). Then, along with the movement of the operator, a position of the marker 29a is moved from a position by dotted lines to a position by solid lines. That is, the position of the marker 29a is largely shifted in a shown y-direction, i.e., in a height direction.

In contrast to this, a position of the mobile X-ray apparatus 1 tracking the operator is not shifted in the y-direction. That is, the position of the video camera 23a is not also shifted in the y-direction. Consequently, a coordinate of the two-dimensional code 31 shown up on the image M is largely shifted before and after the operator Co climbs up and down the stairs (FIGS. 9(b) and 9(c)). That is, a variation in coordinate in the y-direction of the two-dimensional code 31 shown up on the image M is an index for determining that the operator Co has gone to the stairs.

However, the coordinate of the two-dimensional code 31 in the y-direction shown up on the image M also changes largely when the operator Co leans because the operator Co drops and picks up goods. As a result, a large variation in the coordinate of the two-dimensional code 31 in the y-direction does not always mean that the operator Co has gone to the stairs. On the other hand, when the operator Co leans, the operator Co returns to an original attitude for a short period of time. Accordingly, the coordinate of the two-dimensional code 31 in the y-direction is to return for a short period of time.

Consequently, when the position of the two-dimensional code 31 shown up on the image M is changed in the y-direction by a given value or more, the image processor 35 identifies this change and outputs a signal to the control circuit 37. The control circuit 37 stops rotation of the drive wheels 5 temporarily in accordance with the outputted signal. That is because it is a risk to perform continuous automatic tracking of the mobile X-ray apparatus 1 in both cases when the operator Co leans and when the operator Co goes to the stairs.

When the coordinate of the two-dimensional code 31 in the y-direction shown up on the image M is returned within a given period of time, the image processor 35 determines that the operator Co leans temporarily. Then the image processor 35 causes the control circuit 37 to rotate the drive wheels 5 again for restarting the automatic tracking of the mobile X-ray apparatus 1.

On the other hand, when the coordinate of the two-dimensional code 31 in the y-direction shown up on the image M fails to return back to its original within a given period of time, the image processor 35 determines that the operator Co has gone to the stairs. Then the image processor 35 causes the control circuit 37 to output a signal to the input-output terminal 33. The input-output terminal 33 sounds an alert in accordance with the signal outputted from the control circuit 37 for notifying the operator Co that the automatic tracking mode is cancelled due to entering into the no-entry area. With the above configuration, even when the operator Co accidentally climbs up and down the stairs, the mobile X-ray apparatus 1 is able to prevent travelling to the stairs automatically. This achieves operation of the mobile X-ray apparatus 1 with more safety.

In addition, the following describes a function of cancelling the automatic tracking mode in another case when the mobile X-ray apparatus 1 Embodiment 1 enters into the no-entry area with reference to the block diagram of FIG. 4.

Firstly, when no two-dimensional marker 31 is shown up on the image M captured by the video camera 23 for a given period of time, the image processor 35 determines to lose sight of the operator Co, and outputs a signal to the control circuit 37. The control circuit 37 stops rotation of the drive wheels 5 in accordance with the outputted signal, and cancels the automatic tracking mode. Simultaneously, the control circuit 37 sounds an alert to the input-output terminal 33 to notify the operator Co that the automatic tracking mode is cancelled due to loss of the sight of the operator Co. With such a configuration, the mobile X-ray apparatus 1 allows continuous automatic travelling although the mobile X-ray apparatus 1 fails to track the operator Co.

Thereafter, when the operator Co controls any one of the operating handles 21, the pressure sensor inside of the operating handle 21 outputs a signal to the control circuit 37. The control circuit 37 cancels the automatic tracking mode in accordance with the outputted signal. Such a configuration allows the operator Co to assign higher priority to operation with the operating handle 21 than the operation in the automatic tracking mode.

Moreover, when any of the contact sensors 25 detects contact to the obstruction, the contact sensor 25 having detected the obstruction outputs a signal to the control circuit 37. The control circuit 37 cancels the automatic tracking mode in accordance with the outputted signal. Simultaneously, the control circuit 37 sounds an alert to the input-output terminal 33 for notifying the operator Co that the automatic tracking mode is cancelled due to contact to the obstruction. Such a configuration allows rapid cancellation of the automatic tracking mode when the mobile X-ray apparatus 1 contacts to the obstruction, leading to prevention of a dangerous situation.

Finally, the operator Co operates the console panel 19 or the input-output terminal 33 manually, thereby causing the control circuit 37 to cancel the automatic tracking mode at any time. With such a configuration, when the automatic tracking mode of the mobile X-ray apparatus 1 is to be cancelled, the operator Co allows rapid cancellation of the automatic tracking mode for securing safety.

<Effect of Embodiment 1>

The mobile X-ray apparatus according to Embodiment 1 images the operator with the marker by the video camera. Then, the mobile X-ray apparatus automatically travels while tracking the operator from behind in accordance with the two-dimensional code of the marker shown up on the captured image. That is, the operator is able to go rounds while walking frontward of the mobile X-ray apparatus without controlling the operating handles by hands. In other words, upon the rounds with the mobile X-ray apparatus according to Embodiment 1, the operator is able to carry charts, X-ray radiography films and diagnosis tools by hands. Consequently, more patients are able to undergo diagnosis at one round, and wide-ranging diagnosis is obtainable.

In addition, the mobile X-ray apparatus according to Embodiment 1 allows the operator to go rounds while walking frontward of the carriage. This prevents the mobile X-ray apparatus from obstructing a front field of view of the operator. Consequently, the operator allows rapid confirmation of patients and obstructions in advance that come and go, achieving more safe rounds without contacting the mobile X-ray apparatus to the obstructions.

Embodiment 2

The following describes Preferred Embodiment 2 of the present invention with reference to drawings. Like numerals are used to identify like components which are the same as in Embodiment 1 and will not particularly be described.

A mobile X-ray apparatus 1A according to Embodiment 2 includes an optical sensor 39 on a front bottom of the carriage 3. As illustrated in FIG. 10(a), the metal sensors 27 are disposed on both faces of the front bottom of the carriage 3, whereas the optical sensor 39 is disposed at a middle part of the front bottom of the carriage 3. Here, the optical sensor 39 corresponds to the moving route detector in the present invention.

In the automatic tracking mode of the mobile X-ray apparatus 1A, the optical sensor 39 detects a colored tape L laid on the floor, and outputs a signal to the control circuit 37 as in FIG. 4. The control circuit 37 controls the rotation speeds of the drive wheels 5 in accordance with the outputted signal so as for mobile X-ray apparatus 1A to move while tracing the laid colored tape L.

In the mobile X-ray apparatus 1A, higher priority is assigned to the signal outputted from the optical sensor 39 than the signal outputted from the image processor 35. That is, the mobile X-ray apparatus 1A assigns higher priority to a route having the colored tape L laid thereon than to a route calculated from the image M captured by the video camera 23.

Here, the colored tape L is different in color than the floor, and is laid at the middle of the corridor or the intersection as in FIG. 10(b). That is, the mobile X-ray apparatus 1A automatically travels while tracing the colored tape L at the middle in the area with the colored tape L laid thereon regardless of motion of the operator Co. That is, the mobile X-ray apparatus 1A travels along the route on which the colored tape L is laid without tracking the operator Co from behind even when the operator Co turns the corner along the corridor wall. Consequently, this eliminates the possibility that the mobile X-ray apparatus 1A tracks the operator Co and travels to the position by dotted lines to collide against the wall.

In addition, although the operator Co tottering rightward/leftward, the mobile X-ray apparatus 1A is controlled so as to assigning higher priority to the route on which the colored tape L is laid a higher priority than to the route calculated from the two-dimensional code 31 in the image M. That is, the mobile X-ray apparatus 1A moves along a route set in advance regardless of the motion of the operator Co. As a result, this significantly reduces a risk that the mobile X-ray apparatus 1A contacts the coming and going patients or the obstructions. Moreover, in an area with no colored tape L, the mobile X-ray apparatus 1A automatically travels while tracking the operator Co in accordance with the two-dimensional code 31 shown up on the image M, which is similar to the case in Embodiment 1. With the above configuration, the mobile X-ray apparatus 1A according to Embodiment 2 allows automatic tracking along a moving route in a safer manner.

The present invention is not limited to the foregoing examples, but may be modified as follows.

(1) In the embodiments mentioned above, the marker with the two-dimensional code is attached to the operator, and the video camera captures the marker for identifying the position of the operator. However, this is not limitative. Specifically, an ultrasonic oscillator and an ultrasonic sensor may be provided in the mobile X-ray apparatus instead of the video camera, and ultrasonic reflectors may be attached as the labels to the back and shoulders of the operator instead of the markers. The ultrasonic reflectors reflect ultrasonic from the ultrasonic oscillator, and the ultrasonic sensor detects the ultrasonic. That is, the ultrasonic sensor allows calculation of a distance between the operator and the mobile X-ray apparatus, a coordinate of the operator relative to the mobile X-ray apparatus, and a direction of the operator based on a period of time for which the oscillated ultrasonic is reflected.

(2) In the embodiments mentioned above, the input-output terminal is used for notifying the operator that the automatic tracking mode is cancelled. However, this is not limitative. That is, instead of the input-output terminal carried by the operator, an external output speaker may be provided inside the carriage. The external output speaker sounds an alert in accordance with the signal outputted from the control circuit for notifying the operator that the automatic tracking mode is cancelled. Such a configuration leads to no necessity for the operator to carry the input-output terminal. This allows rounds with reduced pieces of baggage.

(3) In the embodiments mentioned above, the metal tape is laid on the boundary on the floor and the metal sensors detect entering into the no-entry area. However, this is not limitative. That is, a colored tape different in color from the boundary on the floor may be laid, and the optical sensor may detect the colored tape.

(4) In the embodiments mentioned above, the operator notices cancellation of the automatic tracking mode via the alert. However, this is not limitative. That is, the input-output terminal may include a vibrating function for notifying the operator via vibration. Such a case never leads the alert as noise around.

(5) In the embodiments mentioned above, the console panel or the input-output terminal is manually operated to cancel the automatic tracking mode at any time. However, this is not limitative. That is, the automatic tracking mode may be cancelled at any time via sound input operation.

(6) In the Embodiment 2, the colored tape is laid on the floor as the moving route and the optical sensor detects the colored tape such that the mobile X-ray apparatus performs automatic tracking while tracing the colored tape. However, this is not limitative. That is, the metal tape may be laid on the floor as the moving route, and the metal sensor may detect the metal tape.

REFERENCE SIGN LIST 1, 1A . . . mobile X-ray apparatus
3 . . . carriage
5 . . . drive wheel
15 . . . X-ray tube
19 . . . console panel
23 . . . video camera (label detector)
25 . . . contact sensor (obstruction detector)
27 . . . metal sensor (laid object detector)
29 . . . marker (label)
31 . . . two-dimensional code
33 . . . input-output terminal (alert sounding device)
35 . . . image processor
37 . . . control circuit (label tracking controller)
39 . . . optical sensor (moving route detector)
K . . . metal tape
L . . . colored tape

The invention claimed is:

1. A mobile X-ray apparatus, comprising:
a carriage of which a main body of the X-ray apparatus is on board;
drive wheels that move the carriage;
a label attached to an operator;
a label detector that detects the label; and
a label tracking controller that controls driving of the drive wheels such that the carriage tracks the label in accordance with a result detected by the label detector.

2. The mobile X-ray apparatus according to claim 1 wherein
the label tracking controller stops the driving of the drive wheels when the label detector detects that the label is moved vertically for a given period of time.

3. The mobile X-ray apparatus according to claim 1, further comprising:
an alert sounding device that sounds an alert, wherein
the alert sounding device sounds the alert when the label detector detects no label for a given period of time.

4. The mobile X-ray apparatus according to claim 3, further comprising:
a laid object detector that detects a laid object that is laid on the floor, wherein
the label tracking controller stops the driving of the drive wheels when the laid object detector detects the laid object.

5. The mobile X-ray apparatus according to claim 4, wherein
the alert sounding device sounds the alert when the laid object detector detects the laid object.

6. The mobile X-ray apparatus according to claim 3, further comprising:

an obstruction detector that detects contact of the carriage to an obstruction, wherein the label tracking controller stops the driving of the drive wheels when the obstruction detector detects the contact of the carriage to the obstruction.

7. The mobile X-ray apparatus according to claim 6, wherein the alert sounding device sounds the alert when the obstruction detector detects the contact of the carriage to the obstruction.

8. The mobile X-ray apparatus according to claim 3, wherein the alert sounding device is a portable terminal.

9. The mobile X-ray apparatus according to claim 1, further comprising:

a moving route detector that detects a moving route of the carriage set in advance, wherein the label tracking controller stops the driving of the drive wheels so as to travel along the moving route when the moving route detector detects the moving route.

* * * * *